(12) United States Patent
Kang et al.

(10) Patent No.: US 9,161,900 B2
(45) Date of Patent: Oct. 20, 2015

(54) COSMETIC COMPOSITION FOR INHIBITING HAIR LOSS AND ENHANCED HAIR GROWTH

(75) Inventors: Byung Ha Kang, Gyeonggi-do (KR); Woori Bae, Gyeonggi-do (KR); Su Na Kim, Gyeonggi-do (KR); Ah Reum Kim, Gyeonggi-do (KR); Kyoung Mi Jung, Gyeonggi-do (KR); Eun Joo Kim, Gyeonggi-do (KR); John Hwan Lee, Gyeonggi-do (KR)

(73) Assignee: AMOREPACIFIC CORPORATION, Seoul (KR)

( * ) Notice: Subject to any disclaimer, the term of this patent is extended or adjusted under 35 U.S.C. 154(b) by 287 days.

(21) Appl. No.: 13/440,533

(22) Filed: Apr. 5, 2012

(65) Prior Publication Data

US 2013/0089632 A1      Apr. 11, 2013

(30) Foreign Application Priority Data

Oct. 5, 2011   (KR) ........................ 10-2011-0101270

(51) Int. Cl.
| | |
|---|---|
| *A61K 36/539* | (2006.01) |
| *A61K 36/13* | (2006.01) |
| *A61K 36/00* | (2006.01) |
| *A61K 36/484* | (2006.01) |
| *A61K 8/97* | (2006.01) |
| *A61Q 7/00* | (2006.01) |

(52) U.S. Cl.
CPC ................ *A61K 8/97* (2013.01); *A61K 36/484* (2013.01); *A61K 36/539* (2013.01); *A61Q 7/00* (2013.01)

(58) Field of Classification Search
CPC .................................................. A61K 36/539
See application file for complete search history.

(56) References Cited

U.S. PATENT DOCUMENTS 5,443,839 A *   8/1995   Meybeck ...................... 424/450
2008/0260867 A1 * 10/2008   Nam .......................... 424/725.1

FOREIGN PATENT DOCUMENTS

JP      04103518 A  *  4/1992

OTHER PUBLICATIONS

Ohkoshi et al. (2009) J. Chromatography A vol. 1216, Issue 11, pp. 2192-2194.*
Website document entitled "Minoxidil Once Daily Topicals to enhance Laser Hair Therapy". (Available at http://laser.hairgrowthcenters.com/?Tag=Licorice%20Root%20Extract). Downloaded from website Dec. 11, 2013.*
Ohkoshi et al. (2009) Journal of Chromatography A, 1216: 2192-2194.*
Tian et al. (2008) Int. J. Mol. Sci. 9, 571-577.*

* cited by examiner

*Primary Examiner* — Chris R Tate
*Assistant Examiner* — Russell Fiebig
(74) *Attorney, Agent, or Firm* — Jansson Munger McKinley & Shape Ltd.

(57) ABSTRACT

The present disclosure provides a cosmetic composition which includes at least one of *Scutellaria baicalensis* essence, licorice essence, and mixture of *Scutellaria baicalensis* extract and licorice extract as active ingredient and, optionally, further includes at least one of zinc pyrithione, panthenol and *thuja* semen extract. The cosmetic composition of the present disclosure is capable of inhibiting hair loss and enhancing hair growth by inhibiting binding with the androgen receptor and regulating the hair growth factor so as to induce transition from telogen to anagen and prolong anagen.

3 Claims, 2 Drawing Sheets

COSMETIC COMPOSITION FOR INHIBITING HAIR LOSS AND ENHANCED HAIR GROWTH

CROSS REFERENCE TO RELATED APPLICATION

This application claims priority based on Korean patent application KR 10-2011-0101270, filed Oct. 5, 2011.

FIELD OF THE INVENTION

The present disclosure relates to a cosmetic composition for inhibiting hair loss or enhancing hair growth, and more particularly to a cosmetic composition for inhibiting hair loss or enhancing hair growth including at least one of *Scutellaria baicalensis* essence, licorice essence, and mixture of *Scutellaria baicalensis* extract and licorice extract as active ingredient.

BACKGROUND OF THE INVENTION

Hair is generated with skin and the hair growth cycle consists of anagen (3-5 years), catagen (1-2 months) and telogen (3-5 months). During the anagen phase, the dermis and the hypodermis are developed. Hair follicles grow in the papillary dermis of the dermis. During the catagen phase, the hair follicles come closer to the epidermis as the thickness of the dermis decreases. Dermal papilla fall off from the hair follicles and a new hair growth cycle begins.

Hair loss can be classified into telogen effluvium and anagen effluvium according to the stage of hair shedding. Telogen effluvium may be caused by the male hormone androgen, childbirth or endocrine disease. Anagen effluvium includes alopecia greata, cicatricial greata and hair loss caused by tinea capitis. Also, focal infection, endocrine disorder, genetic factors, autoimmunity, etc. are known to cause loss of hair.

A variety of signal transduction factors induce hair loss during the hair growth cycle. Growth factors such as Insulin-like growth factor 1 (IGF-1), epidermal growing factor (EGF), fibroblast growth factor (FGF), etc. promote hair growth and prevent death of hair cells, whereas Interleukin-1 (IL-1) and tumor necrosis factor (TNF) cause hair loss by inducing death of hair cells and transforming growth factor-$\beta$1 (TGF-$\beta$1) inhibits hair growth. Among the male hormones, androgen is known to reduce the hair growth and cause degeneration of hair.

Currently, representative treatments for hair loss include Propecia and minoxidil approved by the USFDA. Although these drugs show obvious clinical effects, they have side effects such as sexual dysfunction and skin irritation and are unavailable or limited for use in women. Recently, natural products which are safe can be used regardless of sex and have been actively explored.

Korean Patent No. 10-0581316 discloses a composition for inhibiting hair kiss and enhancing hair growth, which comprises a herbal extract mixture of Leonurus sibiricus, spikenard, mother chrysanthemum, peach kernel, cornus fruit, cuscuta semen, Schisandra chinensis, atractylodes rhizome, pine needle and Angelica gigas. Korean Patent No. 10-0609210 discloses a shampoo composition for inhibiting hair loss, which comprises ethanol extracts of Angelica gigas root and burdock root wherein $\beta$-sitosterol included in the Angelica gigas root suppresses 5$\alpha$-reductase and inulin included in the burdock root improves blood circulation. Although they show hair loss inhibiting effect clinically, their mechanism action is not clearly understood. (see Korean Patent No. 10-0581316 and Korean Patent No. 10-0609210)

SUMMARY OF THE INVENTION

The present disclosure is directed to providing a cosmetic composition and a method for application of a cosmetic composition to hair and scalp which includes at least one of *Scutellaria baicalensis* essence, licorice essence, and mixture of *Scutellaria baicalensis* extract and licorice extract as active ingredient. In addition, the cosmetic composition for application to hair and scalp may further include at least one of zinc pyrithione, panthenol and *thuja* semen extract for inhibiting hair loss and enhancing hair growth by inhibiting binding with the androgen receptor and inhibiting the activity of the hair growth factor.

In one general aspect, the present disclosure provides a cosmetic composition including at least one of *Scutellaria baicalensis* essence, licorice essence, and mixture of *Scutellaria baicalensis* extract and licorice extract as active ingredient. In an exemplary embodiment of the present disclosure, the *Scutellaria baicalensis* essence may include at least 4 wt % of baicalin based on the total weight of the *Scutellaria baicalensis* essence and the licorice essence may include at least 3 wt % of glycyrrhizic acid based on the total weight of the licorice essence.

In an exemplary embodiment of the present disclosure, the *Scutellaria baicalensis* extract may include 0.01-100 ppm of baicalin and the licorice extract may include 0.01-100 ppm of glycyrrhizic acid.

In an exemplary embodiment of the present disclosure, the composition may further include at least one selected from a group consisting of zinc pyrithione, panthenol and *thuja* semen extract.

In an exemplary embodiment of the present disclosure, the composition may include *Scutellaria baicalensis* essence, licorice essence, zinc pyrithione, panthenol and *thuja* semen extract.

In an exemplary embodiment of the present disclosure, the composition may include *Scutellaria baicalensis* extract, licorice extract, zinc pyrithione, panthenol and *thuja* semen extract.

In an exemplary embodiment of the present disclosure, the composition may be for inhibiting hair loss or enhancing hair growth.

In an exemplary embodiment of the present disclosure, the composition and method may inhibit hair loss or enhance hair growth by inhibiting the activity of the hair growth factor.

In an exemplary embodiment of the present disclosure, the composition and method may inhibit hair loss or enhance hair growth by inhibiting the proliferation of the androgen receptor.

In an exemplary embodiment of the present disclosure, the *Scutellaria baicalensis* essence and the licorice essence may be respectively included in an amount of 0.01-2.0 wt % based on the total weight of the composition.

In an exemplary embodiment of the present disclosure, the *Scutellaria baicalensis* extract and the licorice extract may be respectively included in an amount of 0.01-2.0 wt % based on the total weight of the composition.

In an exemplary embodiment of the present disclosure, the zinc pyrithione may be included in an amount of 0.01-2.0 wt % based on the total weight of the composition.

In an exemplary embodiment of the present disclosure, the panthenol may be included in an amount of 0.01-2.0 wt % based on the total weight of the composition.

In an exemplary embodiment of the present disclosure, the *thuja* semen extract may be included in an amount of 0.01-2.0 wt % based on the total weight of the composition.

DETAILED DESCRIPTION OF THE INVENTION

Hereinafter, exemplary embodiments will be described in detail with reference to the accompanying drawings.

The present disclosure provides a cosmetic composition and a method for applying a cosmetic composition comprising at least one of *Scutellaria baicalensis* essence, licorice essence, and mixture of *Scutellaria baicalensis* extract and licorice extract as active ingredient.

The composition may further comprise at least one selected from a group consisting of zinc pyrithione, panthenol and *thuja* semen extract. More specifically, the composition may comprise *Scutellaria baicalensis* essence, licorice essence, zinc pyrithione, panthenol and *thuja* semen extract. Also, it may comprise *Scutellaria baicalensis* extract, licorice extract, zinc pyrithione, panthenol and *thuja* semen extract.

The cosmetic composition according to the present disclosure may be for inhibiting hair loss or enhancing hair growth. The composition may inhibit hair loss or enhance hair growth by inhibiting the activity of the hair growth factor. Also, the composition may inhibit hair loss or enhance hair growth by inhibiting the proliferation of the androgen receptor. Test examples below disclose the effect.

The Korean Pharmacopoeia defines essence as a preparation obtained by concentrating a herb leachate. It is prepared by leaching herb by cold leaching or hot leaching after adding a leaching agent, followed by filtration and concentration or drying. The pharmacopoeia also prescribes that, differently from normal extracts, the essence contains the main ingredient of the herb with a specific content. Whereas the normal extract contains the main ingredient in a trace amount of several ppm and a large amount of water such that the weight after drying is only 2-3% or less, the essence contains the main ingredient in an amount of several % or more, with the weight after drying up to 50%. That is to say, the essence is highly concentrated and has a high content of thousands to tens of thousands times that of the normal extract.

The *Scutellaria baicalensis* essence may contain 4 wt % or more, specifically 4-30 wt %, of baicalin as main ingredient.

The main ingredient baicalin of the *Scutellaria baicalensis* essence is represented by the chemical formula 1:

(1)

*Scutellaria baicalensis* Georgi is a perennial herb in the Lamiaceae family. The root of *Scutellaria baicalensis* is used as medicine. In Oriental medicine, *Scutellaria baicalensis* is frequently prescribed for the people who have high body temperatures and feel fever and severe thirst. According to the External Medicine chapter of Dongui Bogam, "Those who go bald or lose hair when young tend to have dry blood owing to strong fire." Indeed, more than 90% of those with male pattern baldness suffer from inflammatory conditions on the scalp such as fever and troubles. Accordingly, *Scutellaria baicalensis* having fever-relieving effect is prescribed for many patients with hair loss and antifebrile prescriptions such as Xie Jin Dan described in Jing Yue Quan Shu and Samulhaegitang described in Dongui Bogam contain *Scutellaria baicalensis*.

The *Scutellaria baicalensis* essence used in the present disclosure may be extracted in various ways or purchased. The *Scutellaria baicalensis* essence may be extracted by the commonly employed method. Also, commercially available *Scutellaria baicalensis* essence may be purchased for use. For example, the *Scutellaria baicalensis* essence may be prepared in the following manner. Distilled water (10 L) is added to dried *Scutellaria baicalensis* (1 kg) and reflux extraction is performed 3 times for at least 2 hours at 70-100° C. Then, following sedimentation at 15° C. for 1 day and separation of filtrate and residue via filtration through filter cloth and centrifugation, the separated filtrate is concentrated under reduced pressure at 60° C. or below to obtain 400 g of *Scutellaria baicalensis* extract. The obtained *Scutellaria baicalensis* extract has weight after drying of between 36% and 54%. It is finally sterilized at 121° C. for 30 minutes to obtain the *Scutellaria baicalensis* essence. Thus prepared *Scutellaria baicalensis* essence may comprise 4 wt % or more of baicalin as main ingredient.

In the present disclosure, the *Scutellaria baicalensis* essence may be included in an amount of 0.01-2.0 wt % based on the total weight of the composition for inhibiting hair loss and enhancing hair growth. When the content of the *Scutellaria baicalensis* essence is less than 0.01 wt %, the desired effect may be only slight. And, when the content exceeds 2 wt %, safety problems such as scalp irritation and trouble are likely to occur.

The licorice essence may contain 3 wt % or more, specifically 3-30 wt %, of glycyrrhizic acid as main ingredient.

The main ingredient glycyrrhizic acid of the licorice essence is represented by the chemical formula 2:

(2)

Licorice belongs to the Fabaceae family. In Korea and Japan, the root and stem of licorice (*Glycyrrhiza uralensis* Fischer), European licorice (*Glycyrrhiza glabra* L.) or other plants of the same genus are used with or without the bark removed. In China, the dried root of *Glycyrrhiza uralensis* Fischer, *Glycyrrhiza glabra* L. or *Glycyrrhiza inflata* Batal is used. In Oriental medicine, licorice is known to improve the medicinal efficacy of other medicine by harmonizing the effect thereof and to improve blood circulation by controlling chillness, fever and poison of internal organs. Since it has anti-inflammatory effect, it is prescribed for dermatitis, eczema, peptic ulcer, or the like.

Si Jun Zi Tang described in Yi Fang Ji Jie or Si Ni Tang described in Yixue Rumen includes licorice. Si Jun Zi Tang is known to be effective for hair loss and Si Ni Tang is prescribed for hair dryness.

The licorice essence used in the present disclosure may be extracted in various ways or purchased. The licorice essence may be extracted by the commonly employed method. Also, commercially available licorice essence may be used. For example, the licorice essence may be prepared as follows. Dried licorice (1 kg) is cut and crushed into appropriate size and, after adding purified water (5 L), macerated at room temperature for at least 48 hours. Then, after separating filtrate and residue using cotton filter cloth, followed by concentration under reduced pressure at 60° C. or below, the product is macerated again for 12 hours by adding purified water (3 L) and filtered through cotton filter cloth. This procedure is repeated 3 times. Thus obtained filtrate is combined and concentrated under reduced pressure to a total volume of 3 L. After adding ethanol (1 L), keeping at cool place for at least 48 hours, residue and filtrate are separated by filtering through cotton filter cloth. The obtained filtrate is concentrated under reduced pressure at 60° C. and finally sterilized at 121° C. for 30 minutes to obtain the licorice essence. Thus prepared licorice essence may comprise 3 wt % or more, more specifically 4 wt % or more, of glycyrrhizic acid as main ingredient.

In the present disclosure, the licorice essence may be included in an amount of 0.01-2.0 wt % based on the total weight of the composition for inhibiting hair loss and enhancing hair growth. When the content of the licorice essence is less than 0.01 wt %, the desired effect may be only slight. And, when the content exceeds 2 wt %, safety problems such as scalp irritation and trouble are likely to occur.

The *Scutellaria baicalensis* extract and the licorice extract used in the present disclosure may be prepared by the commonly employed extraction method.

The *Scutellaria baicalensis* extract contains baicalin in less content than the *Scutellaria baicalensis* essence and the licorice extract contains glycyrrhizic acid in less content than the licorice essence. The *Scutellaria baicalensis* extract may contain less than 4 wt %, more specifically 0.01-100 ppm, most specifically 1-10 ppm, of baicalin, although the content of the ingredients for general extract varies depending on many conditions such as extracting method and origin of herb etc so not being particularly limited thereto. And, the licorice extract may contain less than 3 wt %, more specifically 0.01-100 ppm, most specifically 1-10 ppm, of glycyrrhizic acid, although not being particularly limited thereto.

A mixture of *Scutellaria baicalensis* extract and licorice extract used in the present disclosure may be either one obtained by extracting *Scutellaria baicalensis* and licorice together or one obtained by extracting *Scutellaria baicalensis* extract and licorice extract separately and mixing them.

Zinc pyrithione used in the present disclosure is represented by the chemical formula 3:

(3)

Zinc pyrithione is an antifungal agent having antifungal effect of inhibiting the growth of the dandruff-causing fungus. It is included in various haircare products such as shampoo, rinse, etc. for treating dandruff and scalp irritation. In the present disclosure, the zinc pyrithione may be included in an amount of 0.01-2.0 wt % based on the total weight of the composition for inhibiting hair loss and enhancing hair growth. When the content of the licorice essence is less than 0.01 wt %, the desired effect may be only slight. And, when the content exceeds 2 wt %, stability problem may occur.

Panthenol used in the present disclosure may either D-panthenol or DL-panthenol and is represented by the chemical formula 4:

(4)

Panthenol, which is an analog of pantothenic acid, is a provitamin of $B_5$. In organisms, it is quickly converted to vitamin $B_5$. In cosmetics, panthenol is commonly used as humectant, emollient and moisturizer. It is used to prevent inflammation and irritation, soften hair and enhance hair strength.

In the present disclosure, the panthenol may be included in an amount of 0.01-2.0 wt % based on the total weight of the composition for inhibiting hair loss and enhancing hair growth. When the content of the licorice essence is less than 0.01 wt %, the desired effect may be only slight. And, when the content exceeds 2 wt %, stability problem may occur.

*Thuja* semen is the seed of *Thuja orientalis* of the Curpressaceae family. It is oval, elliptical or cylindrical in shape, about 3-5 mm long and about 2-3 mm in diameter. According to Dongui Bogam, *thuja* semen is used in Samsenggo to grow lost mustache or hair. It is also included in Si Sheng Bu Lao Dan or Ban Long Wan, which are prescribed for lack of vitality or symptoms of aging. Also, in modern scientific experiments using two animal models, *thuja* semen was proven to have high hair growth activity by regulating the conversion of androgen.

For example, the *thuja* semen extract may be prepared as follows. *Thuja* semen is extracted with 2 equivalent volume of 95% ethanol, filtered, concentrated, and then agitated in 5 equivalent volume of water and 5 equivalent volume of ethyl acetate for phase separation. The ethyl acetate layer is dried with magnesium sulfate, filtered and concentrated to obtain the *thuja* semen extract.

In the present disclosure, the *thuja* semen extract may be included in an amount of 0.01-2.0 wt % based on the total weight of the composition for inhibiting hair loss and enhancing hair growth. When the content of the *thuja* semen extract is less than 0.01 wt %, the desired effect may be only slight. And, when the content exceeds 2 wt %, stability problem may occur.

That is to say, the present disclosure provides a cosmetic composition for application to hair and scalp having hair loss inhibiting effect, which comprises at least one of the *Scutellaria baicalensis* essence that inhibits binding with the androgen receptor, the licorice essence that inhibits the activity of the hair growth factor inducing catagen, the zinc pyrithione that prevents dandruff and hyperkeratinization, the panthenol that provides nutrients to hair, and the *thuja* semen extract that inhibits 5α-reductase.

When the *Scutellaria baicalensis* extract and the licorice extract are included together in the composition of the present disclosure, they provide excellent synergic effect of inhibiting hair loss and enhancing hair growth as compared to when each extract is included alone.

When any one of the *Scutellaria baicalensis* essence and the licorice essence is included alone in the composition of the present disclosure, it provides excellent effect of inhibiting hair loss and enhancing hair growth in case of essence. In addition, when at least one selected from a group consisting of zinc pyrithione, panthenol and *thuja* semen extract is further added to the cosmetic composition comprising at least one of *Scutellaria baicalensis* essence, licorice essence, and mixture of *Scutellaria baicalensis* extract and licorice extract as active ingredient, they provide better effect of inhibiting hair loss and enhancing hair growth as compared to when only one of zinc pyrithione, panthenol and *thuja* semen extract is included or when none of zinc pyrithione, panthenol and *thuja* semen extract is added to one or more of *Scutellaria baicalensis* essence, licorice essence, and mixture of *Scutellaria baicalensis* extract and licorice extract.

The cosmetic composition of the present disclosure is for application to the scalp and hair. The cosmetic composition of the present disclosure may be in the form of hair cleanser, hair lotion, shampoo or rinse, but is not limited thereto.

The cosmetic composition of the present disclosure may further comprise an anionic surfactant. Alkyl sulfate, ethoxylated alkyl sulfate, alkyl ethoxycarboxylate, alkyl glyceryl ether sulfonate, ethoxy ether sulfonate, methyl acyl taurate, alkyl sulfosuccinate, alkyl ethoxysulfosuccinate, α-sulfonated fatty acid, salts and/or esters thereof, alkyl phosphate ester, ethoxylated alkyl phosphate ester, straight-chain alkyl benzenesulfonate, paraffin sulfonate, α-olefin sulfonate, alkyl alkoxysulfate and mixtures thereof may be used as the anionic surfactant. The surfactant may have an alkyl and/or acyl chain which is $C_{12-18}$, specifically $C_{12-14}$, long. When the chain length is shorter than $C_{12}$, surfactant power decreases. And, when the chain length exceeds $C_{18}$, foaming power decreases. In an exemplary embodiment of the present disclosure, the anionic surfactant may be included in an amount of 1-50 wt %, specifically 5-20 wt %, based on the total weight of the composition. When the content is less than 1 wt %, cleansing power may be insufficient. And, when the content exceeds 50 wt %, excessive cleansing power and irritation to the human body are undesirable.

The cosmetic composition of the present disclosure may further comprise a cationic polymer such as polymeric quaternary ammonium salt of hydroxyethyl cellulose, guar hydroxypropyl triammonium chloride, or the like. The cationic polymer conditions hair, smoothens hair surface and improves foaming power. In an exemplary embodiment of the present disclosure, the cationic polymer may be included in an amount of 0.1-1.0 wt %, specifically 0.1-0.5 wt %, based on the total weight of the composition. When the content is less than 0.1 wt %, the desired effects cannot be expected. And, when the content exceeds 1.0 wt %, viscosity control is difficult and the user may feel uncomfortable because of excessive adhesiveness to hair.

The cosmetic composition of the present disclosure may comprise silicone as conditioning ingredient. The silicone for hair conditioning may include cyclomethicone, dimethicone (polydimethylsiloxane), dimethicone copolyol, alkyl dimethicone copolyol, silicone ester, fluorodimethicone, alkyldimethicone, dimethicone copolyolamine, carboxysilicone, silicone phosphate ester, silicone resin, silicone phospholipid, amodimethicone, aminopropyl dimethicone and silicone quartz. The silicone may be included in an amount of 0.01-5.0 wt %, specifically 1.3-3.0 wt %, based on the total weight of the composition. When the content is less than 0.01 wt %, the desired conditioning effect cannot be expected. And, when the content exceeds 5.0 wt %, stability and quality problems may arise.

The composition according to the present disclosure may further comprise pigment, antiseptic, sequestrant, flavor, etc. in an amount not negatively affecting stability.

The examples and experiments will now be described. The following examples and experiments are for illustrative purposes only and not intended to limit the scope of this disclosure.

Comparative Example 1

Preparation of *Scutellaria baicalensis* extract 80% ethanol aqueous solution (5 L) and other ingredients described in Table 1 were added to dried *Scutellaria baicalensis* (1 kg). After performing reflux extraction for 3 times, followed by sedimentation at 15° C. for 1 day, residue and filtrate were separated by filtration through filter cloth and centrifugation. The separated filtrate was concentrated under reduced pressure to obtain *Scutellaria baicalensis* extract.

Comparative Example 2

Preparation of licorice extract 80% ethanol aqueous solution (5 L) and other ingredients described in Table 1 were added to dried licorice (1 kg). After performing reflux extraction for 3 times, followed by sedimentation at 15° C. for 1 day, residue and filtrate were separated by filtration through filter cloth and centrifugation. The separated filtrate was concentrated under reduced pressure to obtain licorice extract.

Example 1

The composition of Example 1 was prepared by adding 0.1 wt % of the *Scutellaria baicalensis* extract prepared in Comparative Example 1 and 0.1 wt % of the licorice extract prepared in Comparative Example 2.

Examples 2-14

The compositions of Examples 2-14 were prepared as described in Table 1.

TABLE 1

| Ingredients | Comp. Ex. 1 | Comp. Ex. 2 | Ex. 1 | Ex. 2 | Ex. 3 | Ex. 4 | Ex. 5 | Ex. 6 | Ex. 7 | Ex. 8 | Ex. 9 | Ex. 10 | Ex. 11 | Ex. 12 | Ex. 13 | Ex. 14 |
|---|---|---|---|---|---|---|---|---|---|---|---|---|---|---|---|---|
| | | | | | | | (unit wt %) | | | | | | | | | |
| Purified water | | | | | | | To 100 | | | | | | | | | |
| *Scutellaria baicalensis* essence | — | — | — | 0.1 | — | 0.1 | — | — | — | 0.1 | — | 0.1 | 0.1 | 0.1 | 0.009 | 2.01 |
| Licorice essence | — | — | — | — | 0.1 | 0.1 | — | — | — | — | 0.1 | 0.1 | 0.1 | 0.1 | 0.009 | 2.01 |
| *Thuja* semen extract | — | — | — | — | — | — | 0.2 | 0.2 | 02 | — | — | 02 | 0.2 | 02 | — | — |

TABLE 1-continued

| Ingredients | Comp. Ex. 1 | Comp. Ex. 2 | Ex. 1 | Ex. 2 | Ex. 3 | Ex. 4 | Ex. 5 | Ex. 6 | Ex. 7 | Ex. 8 | Ex. 9 | Ex. 10 | Ex. 11 | Ex. 12 | Ex. 13 | Ex. 14 |
|---|---|---|---|---|---|---|---|---|---|---|---|---|---|---|---|---|
| | | | | | | | (unit wt %) | | | | | | | | | |
| Zinc pyrithione solution (48%) | — | — | — | — | — | — | — | 0.6 | 0.6 | 0.6 | — | — | 0.6 | 0.6 | — | — |
| Panthenol | — | — | — | — | — | — | — | — | 1 | — | 1 | — | — | 1 | — | — |
| Scutellaria baicalensis extract | 0.1 | — | 0.1 | — | — | — | 0.1 | 0.1 | 0.1 | — | — | — | — | — | — | — |
| Licorice extract | — | 0.1 | 0.1 | — | — | — | 0.1 | 0.1 | 0.1 | — | — | — | — | — | — | — |
| Ammonium lauryl sulfate solution (25%) | 30 | 30 | 30 | 30 | 30 | 30 | 30 | 30 | 30 | 30 | 30 | 30 | 30 | 30 | 30 | 30 |
| Ammonium laureth sulfate solution (25%) | 20 | 20 | 20 | 20 | 20 | 20 | 20 | 20 | 20 | 20 | 20 | 20 | 20 | 20 | 20 | 20 |
| Lauryl dimethyl amine oxide solution (35%) | 5 | 5 | 5 | 5 | 5 | 5 | 5 | 5 | 5 | 5 | 5 | 5 | 5 | 5 | 5 | 5 |
| Cocamide MEA | 1 | 1 | 1 | 1 | 1 | 1 | 1 | 1 | 1 | 1 | 1 | 1 | 1 | 1 | 1 | 1 |
| Cetyl alcohol | 0.5 | 0.5 | 0.5 | 0.5 | 0.5 | 0.5 | 0.5 | 0.5 | 0.5 | 0.5 | 0.5 | 0.5 | 0.5 | 0.5 | 0.5 | 0.5 |
| Polyquaternium 10 | 0.5 | 0.5 | 0.5 | 0.5 | 0.5 | 0.5 | 0.5 | 0.5 | 0.5 | 0.5 | 0.5 | 0.5 | 0.5 | 0.5 | 0.5 | 0.5 |
| Fragrance | 1 | 1 | 1 | 1 | 1 | 1 | 1 | 1 | 1 | 1 | 1 | 1 | 1 | 1 | 1 | 1 |

Test Example 1

Androgen Receptor Inhibition Assay

Androgen receptor inhibition assay was carried out in vitro using LNCaP cells having the androgen receptor and using the compositions of Comparative Examples 1-2 and Examples 1-14.

Since LNCaP cells show increased proliferation when treated with dihydrotestosterone (DHT), DHT was used as negative control. And, since treatment with flutamide reduces proliferation of the cells, the androgen receptor inhibitor flutamide was used as positive control.

The human prostate cancer cell line LNCaP cells were acquired from the American Type Culture Collection (Manassas, Va., USA) and cultured for 24 hours in RPMI 1640 medium containing 10% fetal bovine serum (FBS) and 2 mM 1-glutamine in an incubator maintained at 5% $CO_2$ and 37° C.

The LNCaP cells that had been cultured for 24 hours were treated with the compositions of Comparative Examples 1-2 and Examples 1-14 on a 96-well plate and then cultured for 48 hours in an incubator. Cell viability of the cultured cells was measured using the WST-1 reagent. The result is shown in Table 2 and FIG. 1.

TABLE 2

| | Cell viability (%) |
|---|---|
| Non-treated group | 100 |
| 1 nM DHT | 118.7 |
| 1 μM flutamide | 89.2 |
| Comparative Example 1 | 119.1 |
| Comparative Example 2 | 120.3 |
| Example 1 | 117.4 |
| Example 2 | 98.9 |
| Example 3 | 99.1 |
| Example 4 | 87.2 |
| Example 5 | 116.8 |
| Example 6 | 116.6 |
| Example 7 | 110.9 |
| Example 8 | 95.1 |
| Example 9 | 93.9 |
| Example 10 | 83.1 |
| Example 11 | 80.9 |
| Example 12 | 75.5 |
| Example 13 | 115.1 |
| Example 14 | 88.1 |

Figure 1:
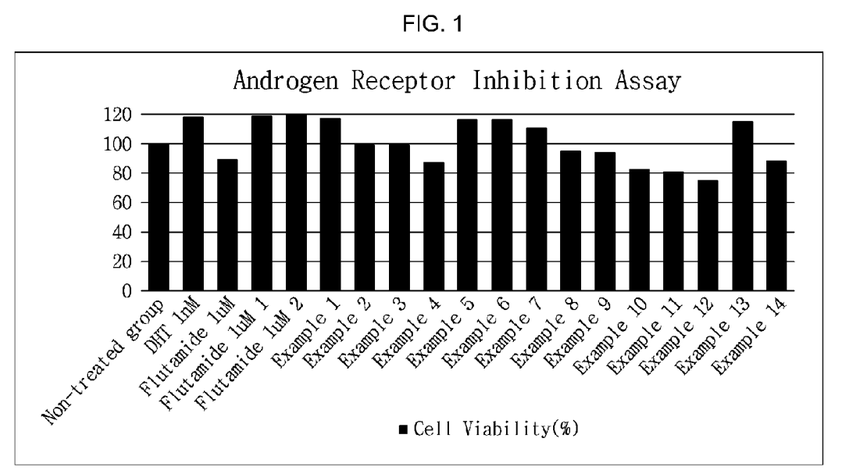
FIG. 1 shows the effect of a composition according to an embodiment of the present disclosure on the binding with the androgen receptor.

As seen from Table 2 and FIG. 1, Examples 2 and 3, in which the cells were treated respectively with the *Scutellaria baicalensis* essence and the licorice essence of the present disclosure, and Example 5, in which the cells were treated with the *Scutellaria baicalensis* essence and the licorice essence at the same time, showed significantly increased inhibition of cell viability as compared to Comparative Examples 1 and 2, in which the cells were treated the *Scutellaria baicalensis* extract and the licorice extract. Examples 10, 11 and 12, in which the cells were further treated respectively with *thuja* semen extract, *thuja* semen extract+zinc pyrithione or *thuja* semen extract+zinc pyrithione+panthenol in addition to the *Scutellaria baicalensis* essence and the licorice essence showed much better inhibition effect. Although Examples 13 and 14 also showed better inhibition effect than Comparative Examples 1 and 2, the best effect was attained when the contents of the *Scutellaria baicalensis* essence and the licorice essence were 0.1 wt %, respectively.

Test Example 2

Activity of Hair Growth Factor

The effect of the compositions of Comparative Examples 1-2 and Examples 1-14 on the activity of hair growth factor TGF-β was tested.

iDPc cells (human immortalized dermal papilla cells) were prepared by transducing human dermal papilla cells into a vector comprising simian virus 40 large T (SV40T) and c-myc. The cells were cultured in Dulbecco's modified Eagle's medium (DMEM; Gibco BRL, Gaithersburg, Md., USA) containing 20% FBS (Hyclone, Logan, Utah).

The iDPc cells were cultured on a 12-well plate for 24 hours in an incubator at 37° C. and then treated with the compositions of Comparative Examples 1-2 and Examples 1-14. 18 hours later, TGF-β inhibition activity was measured using the ELIZA kit (R&D Systems). The result is shown in Table 3 and FIG. 2.

TABLE 3

| | Concentration of human TGF-β (pg/mL) |
|---|---|
| Non-treated group | 2240.31 |
| Comparative Example 1 | 1166.26 |

TABLE 3-continued

|  | Concentration of human TGF-β (pg/mL) |
| --- | --- |
| Comparative Example 2 | 1422.69 |
| Example 1 | 1070.59 |
| Example 2 | 880.55 |
| Example 3 | 890.97 |
| Example 4 | 750.21 |
| Example 5 | 1000.99 |
| Example 6 | 999.87 |
| Example 7 | 954.23 |
| Example 8 | 870.51 |
| Example 9 | 880.99 |
| Example 10 | 740.34 |
| Example 11 | 730.99 |
| Example 12 | 700.78 |
| Example 13 | 900.12 |
| Example 14 | 702.12 |

Figure 2:
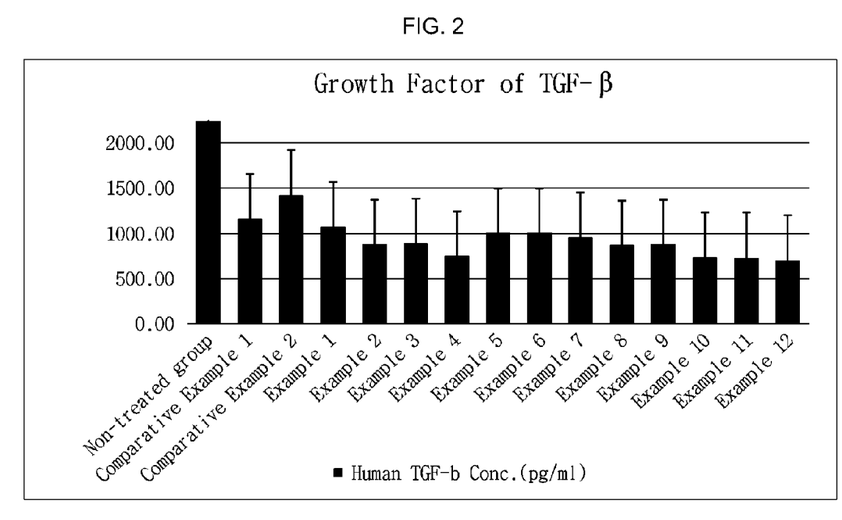
FIG. 2 shows the effect of a composition according to an embodiment of the present disclosure on the hair growth factor.

As seen from Table 3 and FIG. 2, Examples 2 and 3, in which the cells were treated respectively with the *Scutellaria baicalensis* essence and the licorice essence of the present disclosure, and Example 5, in which the cells were treated with the *Scutellaria baicalensis* essence and the licorice essence at the same time, showed significantly increased inhibition of TGF-β, which inhibits hair growth, as compared to Comparative Examples 1 and 2, in which the cells were treated the *Scutellaria baicalensis* extract and the licorice extract. Examples 10, 11 and 12, in which the cells were further treated respectively with *thuja* semen extract, *thuja* semen extract+zinc pyrithione or *thuja* semen extract+zinc pyrithione+panthenol in addition to the *Scutellaria baicalensis* essence and the licorice essence showed much better inhibition effect against TGF-β. Although Examples 13 and 14 also showed better inhibition effect than Comparative Examples 1 and 2, the best effect was attained when the contents of the *Scutellaria baicalensis* essence and the licorice essence were 0.1 wt %, respectively.

Test Example 3

Hair Loss Inhibiting Effect

Hair loss inhibiting effect was tested for 16 weeks on 30 subjects who show early hair loss. After use of the compositions of Comparative Examples 1-2 and Examples 1-14 once a day for 16 weeks, the hairs lost during hair washing were collected and counted. The result is shown in Table 4 and FIG. 3.

TABLE 4

|  | Average number of lost hairs/standard deviation |
| --- | --- |
| Non-treated group | 85.70/10.56 |
| Comparative Example 1 | 84.99/10.54 |
| Comparative Example 2 | 85.30/10.47 |
| Example 1 | 84.23/10.41 |
| Example 2 | 83.12/9.78 |
| Example 3 | 83.95/9.81 |
| Example 4 | 82.24/8.98 |
| Example 5 | 83.99/10.39 |
| Example 6 | 83.77/10.35 |
| Example 7 | 83.75/10.25 |
| Example 8 | 83.09/9.72 |
| Example 9 | 83.88/9.79 |
| Example 10 | 82.03/8.78 |
| Example 11 | 81.86/8.79 |
| Example 12 | 81.23/8.67 |
| Example 13 | 84.77/9.76 |
| Example 14 | 83.55/9.24 |

Figure 3:
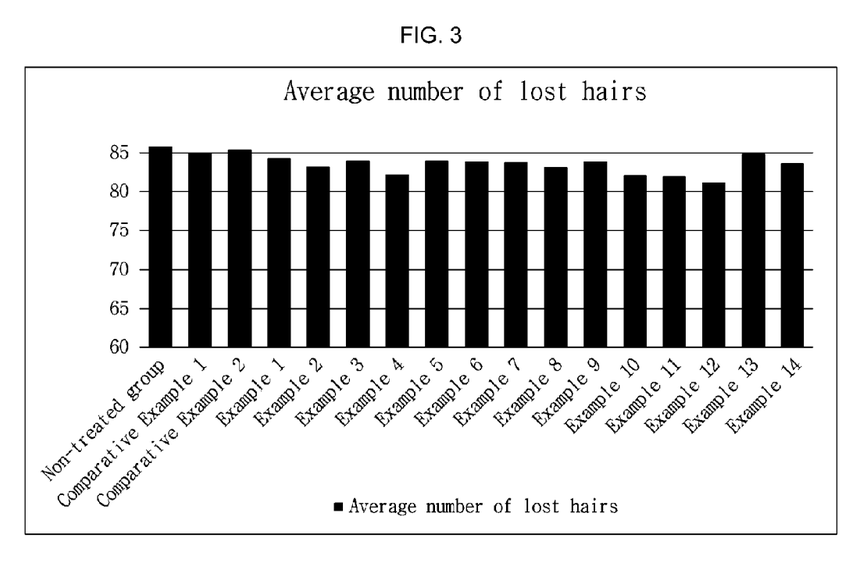
FIG. 3 shows the hair loss inhibiting effect of a composition according to an embodiment of the present disclosure.

As seen from Table 4 and FIG. 3, Examples 2 and 3, in which the cells were treated respectively with the *Scutellaria baicalensis* essence and the licorice essence of the present disclosure, and Example 5, in which the cells were treated with the *Scutellaria baicalensis* essence and the licorice essence at the same time, showed significantly decreased number of lost hairs as compared to Comparative Examples 1 and 2, in which the cells were treated the *Scutellaria baicalensis* extract and the licorice extract. Examples 10, 11 and 12, in which the cells were further treated respectively with *thuja* semen extract, *thuja* semen extract+zinc pyrithione or *thuja* semen extract+zinc pyrithione+panthenol in addition to the *Scutellaria baicalensis* essence and the licorice essence showed much better hair loss inhibition effect. Although Examples 13 and 14 also showed better hair loss inhibition effect than Comparative Examples 1 and 2, the best effect was attained when the contents of the *Scutellaria baicalensis* essence and the licorice essence were 0.1 wt %, respectively.

Test Example 4

Irritation to Eye

Eye irritation test was carried out for the compositions of Comparative Examples 1-2 and Examples 1-14.

The compositions of Comparative Examples 1-2 and Examples 1-14 tested on 16-week-old male rabbits (9 per each group). For the rabbits of non-washed groups, 0.1 mL of test substance was introduced into the conjunctival sac of the right eye and observation was made for lesions in the cornea, iris and conjunctiva on days 1, 2, 3, 4 and 7. The rabbits of washed groups were treated with 0.1 mL of the test substance and the treated eyes were washed 30 seconds later. Eye irritancy of the test substance was evaluated according to Draize's scale for scoring of ocular lesions with reference to Guillot's ocular irritation score index.

The scale for scoring of ocular lesions is described in Table 5. The evaluation result is shown in Table 6 (non-washed groups) and Table 7 (washed groups).

TABLE 5

|  | Score | |
| --- | --- | --- |
|  | I.A.O.I.* | M.I.O.I.** |
| Non-irritating | 0-5 | 0 (after 48 hours) |
| Moderately irritating | 5-15 | ≤5 (after 48 hours) |
| Irritating | 15-30 | ≤5 (after 4 days) |

*I.A.O.I. (index of acute ocular irritation): maximum value of M.I.O.I. on days 1, 2, 3, 4 and 7
**M.I.O.I. (mean index of ocular irritation): sum of scores for each animal for each observation time

TABLE 6

|  | M.I.O.I. | | | | | |
| --- | --- | --- | --- | --- | --- | --- |
| Day | 1 | 2 | 3 | 4 | 7 | I.A.O.I. |
| Non-treated group | 0 | 0 | 0 | 0 | 0 | 0 |
| Comparative Example 1 | 0 | 0 | 0 | 0 | 0 | 0 |
| Comparative Example 2 | 0 | 0 | 0 | 0 | 0 | 0 |
| Example 1 | 0 | 0 | 1 | 1 | 1 | 1 |
| Example 2 | 0 | 0 | 0 | 0 | 0 | 0 |
| Example 3 | 0 | 0 | 0 | 0 | 0 | 0 |
| Example 4 | 0 | 0 | 0 | 0 | 0 | 0 |
| Example 5 | 0 | 0 | 1 | 1 | 1 | 1 |
| Example 6 | 0 | 1 | 1 | 2 | 2 | 3 |
| Example 7 | 0 | 1 | 2 | 2 | 2 | 5 |
| Example 8 | 0 | 0 | 0 | 0 | 1 | 0 |
| Example 9 | 0 | 0 | 0 | 0 | 1 | 0 |

TABLE 6-continued

| Day | M.I.O.I. | | | | | I.A.O.I. |
|---|---|---|---|---|---|---|
| | 1 | 2 | 3 | 4 | 7 | |
| Example 10 | 0 | 0 | 0 | 0 | 0 | 1 |
| Example 11 | 0 | 0 | 0 | 0 | 0 | 1 |
| Example 12 | 0 | 0 | 0 | 0 | 0 | 1 |
| Example 13 | 0 | 0 | 0 | 0 | 0 | 0 |
| Example 14 | 1 | 2 | 3 | 3 | 4 | 1 |

TABLE 7

| Day | M.I.O.I. | | | | | I.A.O.I. |
|---|---|---|---|---|---|---|
| | 1 | 2 | 3 | 4 | 7 | |
| Non-treated group | 0 | 0 | 0 | 0 | 0 | 0 |
| Comparative Example 1 | 0 | 0 | 0 | 0 | 0 | 0 |
| Comparative Example 2 | 0 | 0 | 0 | 0 | 0 | 0 |
| Example 1 | 0 | 0 | 0 | 0 | 0 | 0 |
| Example 2 | 0 | 0 | 0 | 0 | 0 | 0 |
| Example 3 | 0 | 0 | 0 | 0 | 0 | 0 |
| Example 4 | 0 | 0 | 0 | 0 | 0 | 0 |
| Example 5 | 0 | 0 | 0 | 0 | 0 | 0 |
| Example 6 | 0 | 0 | 0 | 1 | 1 | 1 |
| Example 7 | 0 | 0 | 1 | 1 | 1 | 1 |
| Example 8 | 0 | 0 | 0 | 0 | 0 | 0 |
| Example 9 | 0 | 0 | 0 | 0 | 0 | 0 |
| Example 10 | 0 | 0 | 0 | 0 | 0 | 0 |
| Example 11 | 0 | 0 | 0 | 0 | 0 | 0 |
| Example 12 | 0 | 0 | 0 | 0 | 0 | 0 |
| Example 13 | 0 | 0 | 0 | 0 | 0 | 0 |
| Example 14 | 0 | 1 | 1 | 2 | 2 | 8 |

As seen from Table 6, the composition of Example 7 was moderately irritating and the composition of Example 14 was irritating for the non-washed groups. All the other compositions excluding those of Example 7 and Example 14 were non-irritating for the non-washed groups.

And, as seen from Table 7, the composition of the non-treated group, Comparative Examples 1-2 and Example 1-14 were non-irritating for the washed groups.

The composition of Example 14 could also be evaluated as moderately irritating from the I.A.O.T. and M.I.O.I. values.

Formulation Example 1

Preparation of Hair Lotion

Hair lotion was prepared with the following ingredients and contents according to the commonly employed method.

| Ingredients | Contents (%) |
|---|---|
| Beeswax | 4.00 |
| Polysorbate 60 | 1.50 |
| Sorbitan sesquiolate | 0.70 |
| Mineral oil | 4.50 |
| Squalane | 3.00 |
| Isocetyl myristate | 3.50 |
| Caffeine | 0.80 |
| Glycerin | 3.00 |
| Dipropylene glycol | 3.00 |
| Carboxyvinyl polymer | 0.12 |
| Triethanolamine | 0.24 |
| Composition of Example 10 | 1.20 |
| Antiseptic | Adequate |
| Fragrance and pigment | Adequate |
| Purified water | To 100 |

Formulation Example 2

Preparation of Shampoo

Shampoo was prepared with the following ingredients and contents according to the commonly employed method.

| Ingredients | Contents (%) |
|---|---|
| Sodium laureth sulfate | 20.60 |
| Sodium cocoamphoacetate | 14.50 |
| Cocamidopropyl betaine | 4.30 |
| Propylene glycol | 1.50 |
| Caffeine | 0.50 |
| Composition of Example 11 | 0.40 |
| Citric acid | Adequate |
| Antiseptic | Adequate |
| Sodium chloride | Adequate |
| Purified water | To 100 |

The cosmetic composition of the present disclosure is capable of inhibiting hair loss and enhancing hair growth by inhibiting binding with the androgen receptor and regulating the hair growth factor so as to induce transition from telogen to anagen and prolong anagen.

Reference throughout this specification to "the embodiment," "this embodiment," "the previous embodiment," "one embodiment," "an embodiment," "an exemplary embodiment," "another exemplary embodiment," "a preferred embodiment" "another preferred embodiment" or similar language means that a particular feature, structure, or characteristic described in connection with the embodiment is included in at least one embodiment of the present disclosure. Thus, appearances of the phrases "in the embodiment," "in this embodiment," "in the previous embodiment," "in one embodiment," "in an embodiment," "in an exemplary embodiment," "in another exemplary embodiment," "in a preferred embodiment," "in another preferred embodiment," and similar language throughout this specification may, but do not necessarily, all refer to the same embodiment.

Furthermore, the described features, advantages, and characteristics of the disclosure may be combined in any suitable manner in one or more embodiments. One skilled in the relevant art will recognize that the disclosure may be practiced without one or more of the specific features or advantages of a particular embodiment. In other instances, additional features and advantages may be recognized in certain embodiments that may not be present in all embodiments of the disclosure.

While the present disclosure has been described in connection with certain exemplary, preferred or specific embodiments, it is to be understood that the disclosure is not limited to the disclosed embodiments, but, on the contrary, is intended to cover various modifications, alternatives, modifications and equivalent arrangements as will be apparent to those skilled in the art. Any such changes, modifications, alternatives, modifications, equivalents and the like may be made without departing from the spirit and scope of the disclosure.

What is claimed is:

1. A method for inhibiting hair loss or enhancing hair growth comprising topically administering to a subject in need thereof an effective amount of a composition comprising 0.1 to 2.0 wt. % licorice essence and 0.1 to 2.0 wt. % *Scutellaria baicalensis* essence,
   wherein the licorice essence contains at least 3 wt. % glyzyrrhizic acid based on the total weight of the licorice essence, wherein the *Scutellaria baicalensis* essence contains at least 4 wt. % baicalin based on the total weight of the *Scutellaria baicalensis* essence, and wherein the licorice and *Scutellaria baicalensis* essences are each produced by a method comprising the steps of:
- (a) macerating dried licorice root and/or *Scutellaria baicalensis* with water and a leaching agent to obtain a leached licorice root preparation and/or a leached *Scutellaria baicalensis* preparation,
- (b) filtering the leached licorice root and/or *Scutellaria baicalensis* preparation to obtain a filtrate,
- (c) concentrating the filtrate by drying to produce said licorice and *Scutellaria baicalensis* essences.

2. The method for inhibiting hair loss or enhancing hair growth of claim 1, wherein the administered composition inhibits hair loss or enhances hair growth by inhibiting the activity of hair growth factor TGF-$\beta$.

3. The method for inhibiting hair loss or enhancing hair growth of claim 1, wherein the administered composition inhibits hair loss or enhances hair growth by inhibiting proliferation of an androgen receptor.

\* \* \* \* \*